US012582324B2

(12) United States Patent
Heinz et al.

(10) Patent No.: US 12,582,324 B2
(45) Date of Patent: Mar. 24, 2026

(54) LIQUID COUPLED BLOOD PRESSURE SENSOR

(71) Applicant: Verily Life Sciences LLC, South San Francisco, CA (US)

(72) Inventors: David Heinz, Woodside, CA (US); Darien Niamir, Redwood City, CA (US); Michael Allen, Orinda, CA (US)

(73) Assignee: Verily Life Sciences LLC, Dallas, TX (US)

( * ) Notice: Subject to any disclaimer, the term of this patent is extended or adjusted under 35 U.S.C. 154(b) by 850 days.

(21) Appl. No.: 17/890,699

(22) Filed: Aug. 18, 2022

(65) Prior Publication Data

US 2023/0055552 A1 Feb. 23, 2023

Related U.S. Application Data

(60) Provisional application No. 63/234,867, filed on Aug. 19, 2021.

(51) Int. Cl.
*A61B 5/022* (2006.01)
*A61B 5/00* (2006.01)
(Continued)

(52) U.S. Cl.
CPC ...... *A61B 5/02241* (2013.01); *A61B 5/02055* (2013.01); *A61B 5/025* (2013.01);
(Continued)

(58) Field of Classification Search
None
See application file for complete search history.

(56) References Cited

U.S. PATENT DOCUMENTS 3,704,708 A * 12/1972 Iberall ................... A61B 5/021
600/479
5,033,471 A * 7/1991 Yokoe ................ A61B 5/02116
600/494

(Continued)

FOREIGN PATENT DOCUMENTS

DE 102008024737 B3 * 1/2010 ........... A61B 5/0285

OTHER PUBLICATIONS

Translation of DE-102008024737-B3. Retrieved from PE2E Search tool. (Year: 2026).*

(Continued)

*Primary Examiner* — Jacqueline Cheng
*Assistant Examiner* — Samuel C Kim
(74) *Attorney, Agent, or Firm* — Christensen O'Connor Johnson Kindness PLLC

(57) ABSTRACT

A wearable blood pressure meter includes a semi-conformable bladder, serving as a reservoir for an incompressible fluid, and a pressure sensor. The semi-conformable bladder includes a rigid housing defining a cavity within which the incompressible fluid is rigidly constrained and an elastic membrane for elastically constraining the incompressible fluid. The elastic membrane extends across an aperture into the cavity through the rigid housing. The elastic membrane conforms to a body part at the aperture when pressed against the body part. The pressure sensor mechanically couples to the incompressible fluid to measure pressure signals emanating from an artery within the body part and which propagate through the conformable membrane and the incompressible fluid to the pressure sensor.

20 Claims, 11 Drawing Sheets

(51) Int. Cl.
*A61B 5/0205* (2006.01)
*A61B 5/025* (2006.01)
(52) U.S. Cl.
CPC .... *A61B 5/7203* (2013.01); *A61B 2562/0247*
(2013.01); *A61B 2562/168* (2013.01)

(56) References Cited

U.S. PATENT DOCUMENTS

| | | | | |
|---|---|---|---|---|
| 5,316,005 | A * | 5/1994 | Tomita | A61B 5/02208 |
| | | | | 600/499 |
| 5,351,694 | A | 10/1994 | Davis et al. | |
| 5,439,001 | A | 8/1995 | Butterfield et al. | |
| 5,450,852 | A * | 9/1995 | Archibald | A61B 5/02116 |
| | | | | 600/500 |
| 5,722,414 | A | 3/1998 | Archibald et al. | |
| 5,941,828 | A * | 8/1999 | Archibald | A61B 5/6843 |
| | | | | 600/494 |
| 7,232,413 | B2 | 6/2007 | Hashimoto et al. | |
| 7,674,231 | B2 | 3/2010 | McCombie et al. | |
| 8,652,059 | B2 | 2/2014 | Sano et al. | |
| 8,814,800 | B2 | 8/2014 | Fortin et al. | |
| 8,959,745 | B2 | 2/2015 | Ashida | |
| 9,345,424 | B2 | 5/2016 | Wang et al. | |
| 2004/0147956 | A1 * | 7/2004 | Hovanes | A61B 5/0225 |
| | | | | 606/202 |
| 2007/0287923 | A1 * | 12/2007 | Adkins | A61B 5/02438 |
| | | | | 600/485 |
| 2010/0168531 | A1 | 7/2010 | Shaltis et al. | |
| 2011/0160560 | A1 * | 6/2011 | Stone | G01L 9/125 |
| | | | | 600/398 |
| 2012/0010525 | A1 * | 1/2012 | Jacofsky | A61B 5/4519 |
| | | | | 600/561 |
| 2012/0232411 | A1 * | 9/2012 | Brunner | G01F 1/383 |
| | | | | 600/561 |
| 2013/0125613 | A1 * | 5/2013 | Grotov | A61B 5/74 |
| | | | | 73/1.63 |
| 2014/0323891 | A1 | 10/2014 | Sterling et al. | |
| 2015/0080751 | A1 | 3/2015 | Regh et al. | |
| 2015/0272455 | A1 | 10/2015 | Krasnov et al. | |
| 2015/0327784 | A1 | 11/2015 | Lading et al. | |
| 2016/0113589 | A1 | 4/2016 | Yoon | |
| 2016/0198955 | A1 | 7/2016 | Fortin | |
| 2017/0011210 | A1 * | 1/2017 | Cheong | A61B 5/681 |
| 2017/0360306 | A1 | 12/2017 | Narasimhan et al. | |
| 2017/0367597 | A1 | 12/2017 | Fortin | |
| 2018/0206746 | A1 | 7/2018 | Narasimhan et al. | |
| 2019/0090762 | A1 * | 3/2019 | Sawanoi | A61B 5/0225 |
| 2019/0099092 | A1 | 4/2019 | Zhang et al. | |
| 2019/0104953 | A1 | 4/2019 | Narasimhan | |
| 2020/0015689 | A1 | 1/2020 | Allen et al. | |
| 2020/0046278 | A1 * | 2/2020 | Imran | A61B 5/208 |
| 2020/0060561 | A1 | 2/2020 | DeBusschere et al. | |
| 2020/0060847 | A1 * | 2/2020 | Ferguson | A61B 5/103 |

OTHER PUBLICATIONS

International Search Report and Written Opinion, mailed Nov. 24, 2022, in corresponding International Patent Application No. PCT/US2022/040718, 14 pages.
Gizdulich, P., et al., "Models of Brachial to Finger Pulse Wave Distortion and Pressure Decrement," Cardiovascular Research 33:698-705, 1997.
Calhoon, J., "Tactile Sensors Support Next Generation Medical Devices," Aug. 25, 2016, <http://www.designworldonline.com/tactile-sensors-support-next-generation-medical-devices/> [retrieved Jan. 18, 2017], 3 pages.
"The Finapres® Nova," FMS Finapres Medical Systems B.V., brochure, 4 pages.
Bogert, L.W.J., and J.J. van Lieshout, "Non-Invasive Pulsatile Arterial Pressure and Stroke Volume Changes From the Human Finger," Experimental Physiology 90.4:437-446, 2005.

Chen, C.-H., et al., "Estimation of Central Aortic Pressure Waveform by Mathematical Transformation of Radial Tonometry Pressure," Circulation 95:1827-1836, 1997.
Babbs, C.F., "Oscillometric Measurement of Systolic and Diastolic Blood Pressures Validated in a Physiologic Mathematical Model," BioMedical Engineering OnLine 11:56, Dec. 2012, pp. 1-22.
Baker, P.D., et al., "Theoretical Analysis of Non-Invasive Oscillometric Maximum Amplitude Algorithm for Estimating Mean Blood Pressure," Medical and Biological Engineering and Computing 35(3):271-278, May 1997.
Chen, S., et al., "Assessment of Algorithms for Oscillometric Blood Pressure Measurement," Proceedings of the International Instrumentation and Measurement Technology Conference (12MTC 2009), Singapore, May 5-7, 2009, 5 pages.
"Continuous Noninvasive Arterial Pressure," Wikipedia, The Free Encyclopedia <https://en.wikipedia.org/wiki/Continuous_noninvasive_arterial_pressure?oldid+675060442>, 6 pages.
Da Fonseca, L.U.S., et al., "Radial Applanation Tonometry as an Adjuvant Tool in the Noninvasive Arterial Stiffness and Blood Pressure Assessment," World Journal of Cardiovascular Diseases 4(5):225-235, May 2014.
Digiglio, P., et al., "Microflotronic Arterial Tonometry for Continuous Wearable Non-Invasive Hemodynamic Monitoring," Annals of Biomedical Engineering 42(11):2278-2288, Nov. 2014.
Doshi, H., et al., "Does 'Hidden Undercuffing' Occur Among Obese Patients? Effect of Arm Sizes and Other Predictors of the Difference Between Wrist and Upper Arm Blood Pressures," Journal of Clinical Hypertension 12(2):82-88, Feb. 2010.
Drzewiecki, G., et al., "Theory of the Oscillometric Maximum and the Systolic and Diastolic Detection Ratios," Annals of Biomedical Engineering 22(1):88-96, Jan. 1994.
Drzewiecki, G.M., et al., "Arterial Tonometry: Review and Analysis," Journal of Biomechanics 16(2):141-152, 1983.
Forouzanfar, M., et al., "Ratio-Independent Blood Pressure Estimation by Modeling the Oscillometric Waveform Envelope," IEEE Transactions on Instrumentation and Measurement 63(10):2501-2503, Oct. 2014.
"High Blood Pressure," Statistical Fact Sheet, 2014 Update, American Heart Association, 2 pages.
"High Blood Pressure Facts," Centers for Disease Control and Prevention (CDC), Nov. 30, 2016 <https://www.cdc.gov/bloodpressure/facts.htm%5C>, 5 pages.
"Integrated Capacitive Pressure Sensors," Fraunhofer IMS, 2-page brochure.
"Invasive Blood Pressure," © Memscap, Mar. 23, 2018 <http://www.memscap.com/applications-and-market-segments/medical-and-biomedical/invasive-blood-pressure>, 1 page.
Jílek, J., and M. Stork, "The Effect of Wrist Cuff Width on Oscillometric Blood Pressure Waveforms," Electroscope, vol. 2008, No. III, 2008, 4 pages.
Jones, R.D.M., et al., "The Finapres 2300e Finger Cuff: The Influence of Cuff Application on the Accuracy of Blood Pressure Measurement," Anaesthesia 48(7):611-615, Jul. 1993.
Kountz, D.S., et al., "MD Mouse, a New Finger Blood Pressure Monitor, Consistently Underestimates Blood Pressure Compared to a Standard Automatic Syphygnomanometer," Abstract p. 54, Journal of the American Society of Hypertension 9(4S):e35 e48, 2015.
Lan, H., et al., "Effect of Tissue Mechanical Properties on Cuff-Based Blood Pressure Measurements," Medical Engineering and Physics 33(10):1287-1292, Dec. 2011.
Lee, J., and K.C. Nam, "Tonometric Vascular Function Assessment," Chap. 30, in Barros de Mello (ed.), "Biomedical Engineering," Intech Europe, Rijeka, Croatia, 2009, pp. 549-566.
Lee, J., et al., "Comparison Between Dynamic Contour Tonometry and Goldmann Applanation Tonometry," Korean Journal of Ophthalmology 23(1):27-31, Mar. 2009.
Lee, J.Y., et al., "Blood Pressure Measurement Using Finger Cuff," Proceedings of the 27th Annual Conference of IEEE Engineering in Medicine and Biology, Shanghai, Sep. 1-4, 2005, 3 pages.
Liu, J., et al., "Patient-Specific Oscillometric Blood Pressure Measurement," IEEE Transactions on Biomedical Engineering 63(6):1220-1228, Jun. 2016.

(56) References Cited

OTHER PUBLICATIONS

Lyew, M.A., and J.W. Jamieson, "Blood Pressure Measurement Using Oscillometric Finger Cuffs in Children and Young Adults," Anaesthesia 49(10):895-899, Oct. 1994.

McEniery, C.M., et al., "Central Blood Pressure: Current Evidence and Clinical Importance," European Heart Journal 35(26):1719-1725, Jul. 2014.

Miyashita, H., "Clinical Assessment of Central Blood Pressure," Current Hypertension Reviews 8(2):80-90, May 2012.

Ogedegbe, G., and T. Pickering, "Principles and Techniques of Blood Pressure Measurement," Cardiology Clinic 28(4): 71-586, Nov. 2010. (Author Manuscript provided, PMCID:PMC3639494, available in PMC Apr. 30, 2013, 26 pages.).

Pickering, T.G., et al., "Recommendations for Blood Pressure Measurement in Humans and Experimental Animals, Part 1: Blood Pressure Measurement in Humans," Circulation 111(5):697-716, Feb. 2005.

Raamat, R., et al., "Mathematical Modelling of Non-Invasive Oscillometric Finger Mean Blood Pressure Measurement by Maximum Oscillation Criterion," Medical & Biological Engineering & Computing 37(6):784-788, Nov. 1999.

Rosatella, G., et al., "Non Invasive Procedure to Evaluate the Viscoelastic Behavior of the Brachial Artery by Oscillometric Repeated Measurements," Proceedings of the 25th Annual International Conference of the IEEE EMBS, Cancun, Mexico, Sep. 17-21, 2003, pp. 3302-3305.

Schattenkerk, D.W.E., et al., "Nexfin Noninvasive Continuous Blood Pressure Validated Against Riva-Rocci/Korotkoff," American Journal of Hypertension 22(4):378-383, Apr. 2009.

Van Bortel, L.M., et al., "Non-Invasive Assessment of Local Arterial Pulse Pressure: Comparison of Applanation Tonometry and Echo-Tracking," Journal of Hypertension 19(6):1037-1044, Jun. 2001.

International Search Report & Written Opinion mailed on Oct. 4, 2019 for corresponding International Patent Application No. PCT/US2019/04155, 14 pages.

London, Blood-Pressure Monitoring During the COVID-19 Pandemic, https://meritsensor.com/wp-content/uploads/DTXPlus.jpg, Jul. 23, 2020, 3 pages.

DualCap, Disinfection & Protection System, DTXPlus & Safedraw, Disposable Transducer and Closed in-line Sampling System, Merit Medical Brochure, prior to Aug. 18, 2021, 2 pages.

Merit DTXPlus with Safedraw—Set Up, Merit Medical, prior to Aug. 18, 2021, 2 pages.

"Omron HEM-806F Finger Blood Pressure Monitor & Pulse" retrieved from Internet https://www.youtube.com/watch?v=5iCKGCL1s2o, Feb. 27, 2014, 1 page.

"Omron HEM-815F Blood Pressure Monitor Uses Finger", retrieved from Internet https://www.youtube.com/watch?v=b9AbQ2on4p8, Mar. 12, 2009, 1 page.

* cited by examiner

PROXIMAL
PHALANGES 20

PROXIMAL
INTERPHALANGEAL
JOINTS 30

ULNAR SIDE
DIGITAL ARTERY
35

12

11

15

10

RADIAL SIDE
DIGITAL ARTERY
40

METACARPOPHALANGEAL
JOINTS 25

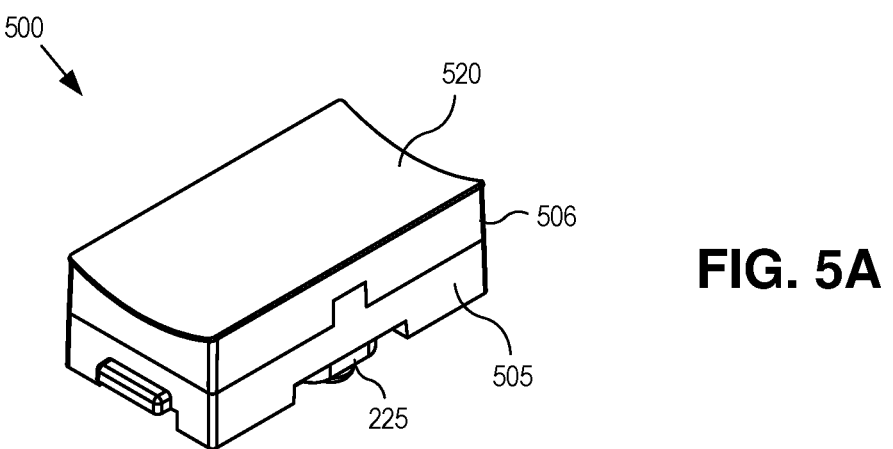
FIG. 5A
FIG. 5B
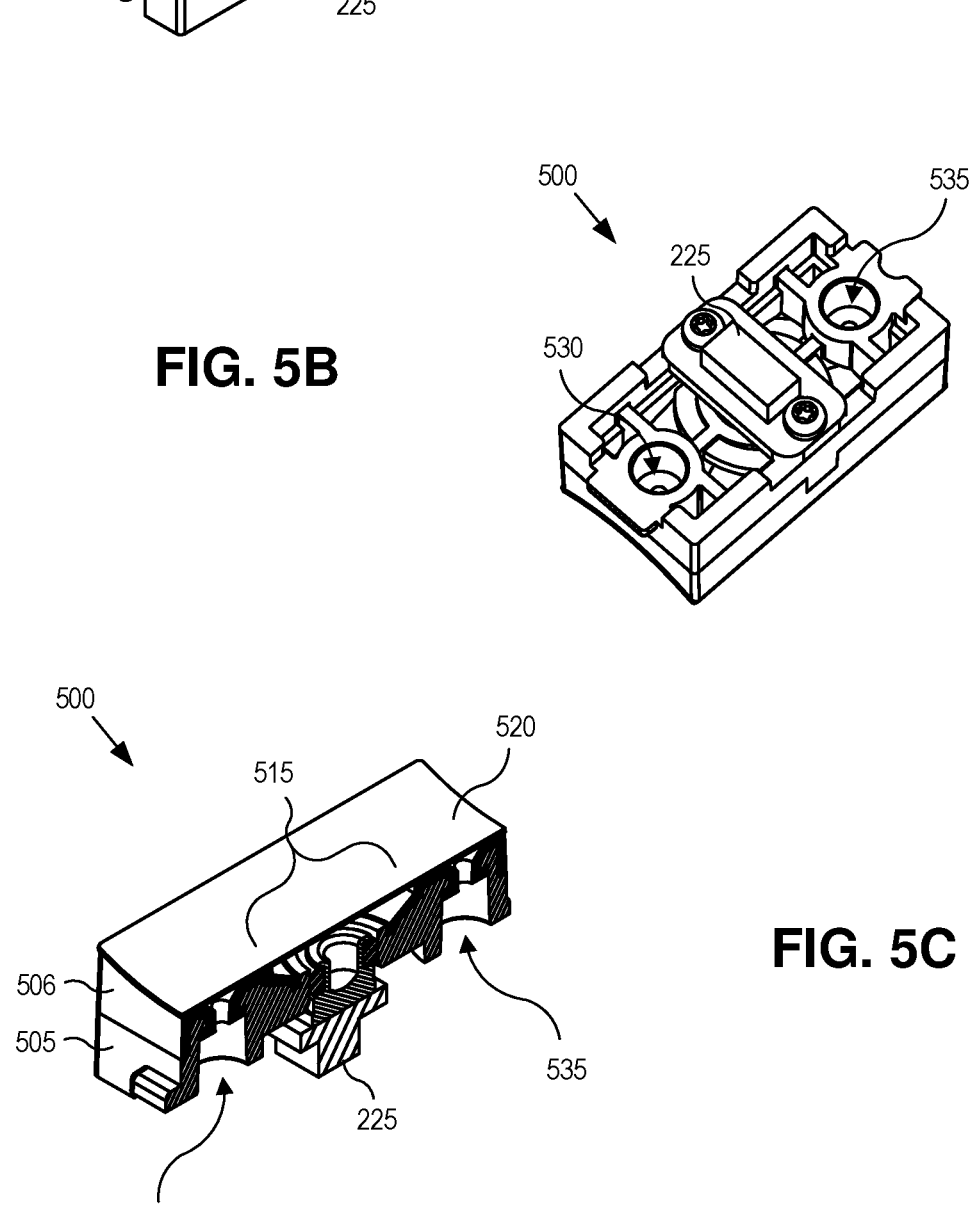
FIG. 5C

LIQUID COUPLED BLOOD PRESSURE SENSOR

CROSS REFERENCE TO RELATED APPLICATIONS

This application claims the benefit of U.S. Application No. 63/234,867, filed on Aug. 19, 2021, the contents of which are incorporated herein by reference.

TECHNICAL FIELD

This disclosure relates generally to blood pressure metering, and in particular but not exclusively, relates to monitoring blood pressure at a digital artery.

BACKGROUND INFORMATION

High blood pressure is a health concern for a large percentage of the population, but regular monitoring is not commonplace. Blood pressure monitors are conventionally found in physician offices, hospitals, pharmacies, and occasionally in homes. However, those who suffer from high blood pressure may only occasionally monitor their blood pressure during a visit to the physician's office or while waiting for a prescription at the pharmacy. Additional monitoring of blood pressure is requested by many physicians, but patients may not follow through due to difficulty in obtaining readings, expense of portable units, or the associated discomfort while using a blood pressure monitor. This discomfort is typically due to squeezing the arm or wrist, for example. Conventional devices that obtain a blood pressure reading from squeezing the arm or wrist typically use an air bladder to both actuate the squeezing and measure the blood pressure signals. However, the air bladder is a poor conductor of the blood pressure signals. Regardless, there is a demand for portable, easy to use, and accurate/sensitive blood pressure monitoring devices.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIGS. 5A-C illustrate front and backside perspective views and a cross-sectional view, respectively, of a semi-conformable bladder, in accordance with a second embodiment of the disclosure.

DETAILED DESCRIPTION

Figure 1A:
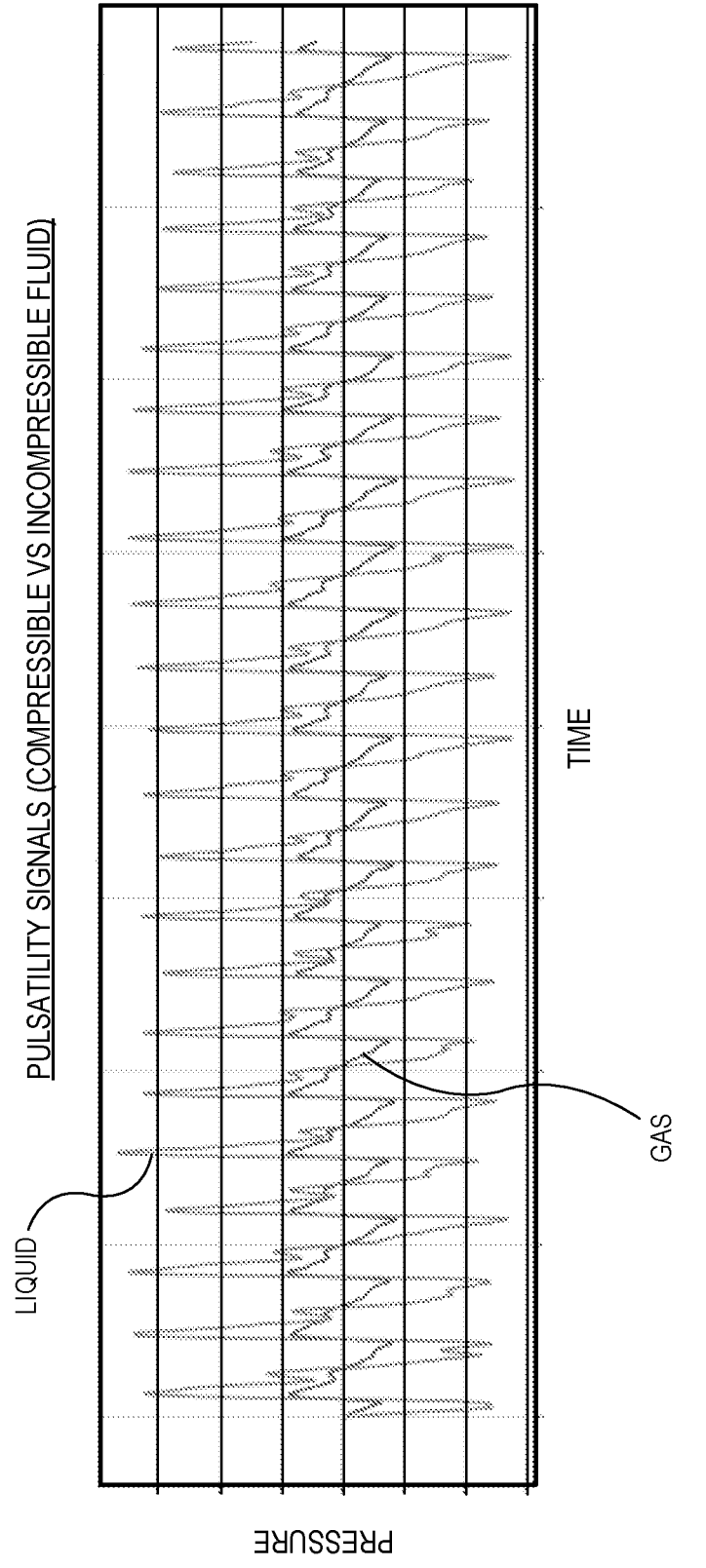
FIG. 1A is a chart comparing signal fidelity between compressible and incompressible fluids operating as the working fluid for transmitting pressure signals between a body part and a pressure sensor, in accordance with an embodiment of the disclosure.

Embodiments of a system, apparatus, and method of operation for a wearable blood pressure meter that couples pressure signals via an incompressible fluid are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Various clinically relevant measurements rely on observation of arterial pressure pulses (referred to herein as "pulsatility signals" or "pressure signals"). For example, blood pressure, cardiac output, heart condition, volume overload, left ventricular end diastolic pressure (LVEDP), fibrillation or arrhythmia can all be monitored via measuring arterial pressure pulses. Conventional observation techniques require the use of an air bladder for coupling between the physiological signal and the sensor. The compressible nature of the air within the bladder dramatically reduces signal coupling, causing a poor signal-to-noise ratio, and resulting in a measurement that is highly susceptible to interferences. Wearable devices suffer from especially poor performance due to geometric/size/weight/power or body location constraints. Embodiments described herein improve upon these drawbacks by using an incompressible fluid (e.g., liquid) to couple the pressure signals emanating from an artery to a pressure sensor. It is anticipated that the techniques described herein for sensing arterial pressure signals may be applicable to other force sensing applications for measuring pressure or monitoring pressure signals beyond just blood pressure. For example, force sensing of button presses and detection of fluid buildup/inflammation in a body part are possible alternative applications. Yet another alternative application may include implementation of a touch screen that can differentiate between multiple different levels/graduations of finger force.

The incompressible fluid reduces damping of the arterial signal via fluid compression and/or elastic expansion of the bladder on sides of the bladder not contacting the skin directly over the artery. Pulsatile energy can be wasted by compressing the compressible fluid, thereby reducing overall signal strength. An incompressible fluid reduces or even prevents this parasitic loss. With a compressible fluid (e.g., such as air), this energy is not only used to change the fluid pressure, but also the volume and temperature of the fluid. In the case of the compressible fluid, pulsatility signals in the artery cause the fluid to reduce in volume and relax local applied pressure. This damps the measured pressure rise relative to the actual arterial pressure increase. An incompressible fluid is unable to reduce in volume, and therefore, the full pressure increase from the arterial pulse is reproduced in the working fluid and can be more readily propagated to and measured by a pressure sensor. Embodiments described herein use a waterproof sensor to meter the incompressible fluid pressure.

FIG. 1A includes a chart comparing measured signal fidelity using a compressible fluid (e.g., gas) vs incompressible fluid (e.g., liquid) as the coupling or working fluid for transmitting pressure signals between a body part including an artery under observation and a pressure sensor. As illustrated, arterial coupling is dramatically improved by using an incompressible fluid. Arterial pulse properties and features (blood pressure, pulse amplitude/rate, dicrotic notch properties, etc.) are better resolved and more accurately measured further empowering blood monitoring devices. Measuring any of these properties by themselves, or their dynamic response to external effects, is more accurate using an incompressible fluid. Thermal effects (e.g. thermal volume expansion of the fluid) are greatly reduced with incompressible fluids, resulting in higher absolute accuracy. The higher speed of sound in incompressible fluids relative to a gas also results in better resolution of high frequency components of the pulsatility signals. Additionally, incompressible fluids or liquids provide improved acoustic impedance match at the skin (e.g., blood and water have nearly identical acoustic impedances), allowing pressure waves and sound to efficiently transfer across the skin-bladder interface with reduced reflections and increased amplitude.

The parasitic losses associated with using a compressible working fluid can be avoided by direct attachment of a pressure sensor to the skin over an artery without use of an intermediary bladder system. However, these direct force sensor arrangements have other drawbacks and reliability issues. For example, the direct force arrangement often induces stress within the sensor substrates as the patient moves, resulting in poor signal reliability.

Figure 1B:
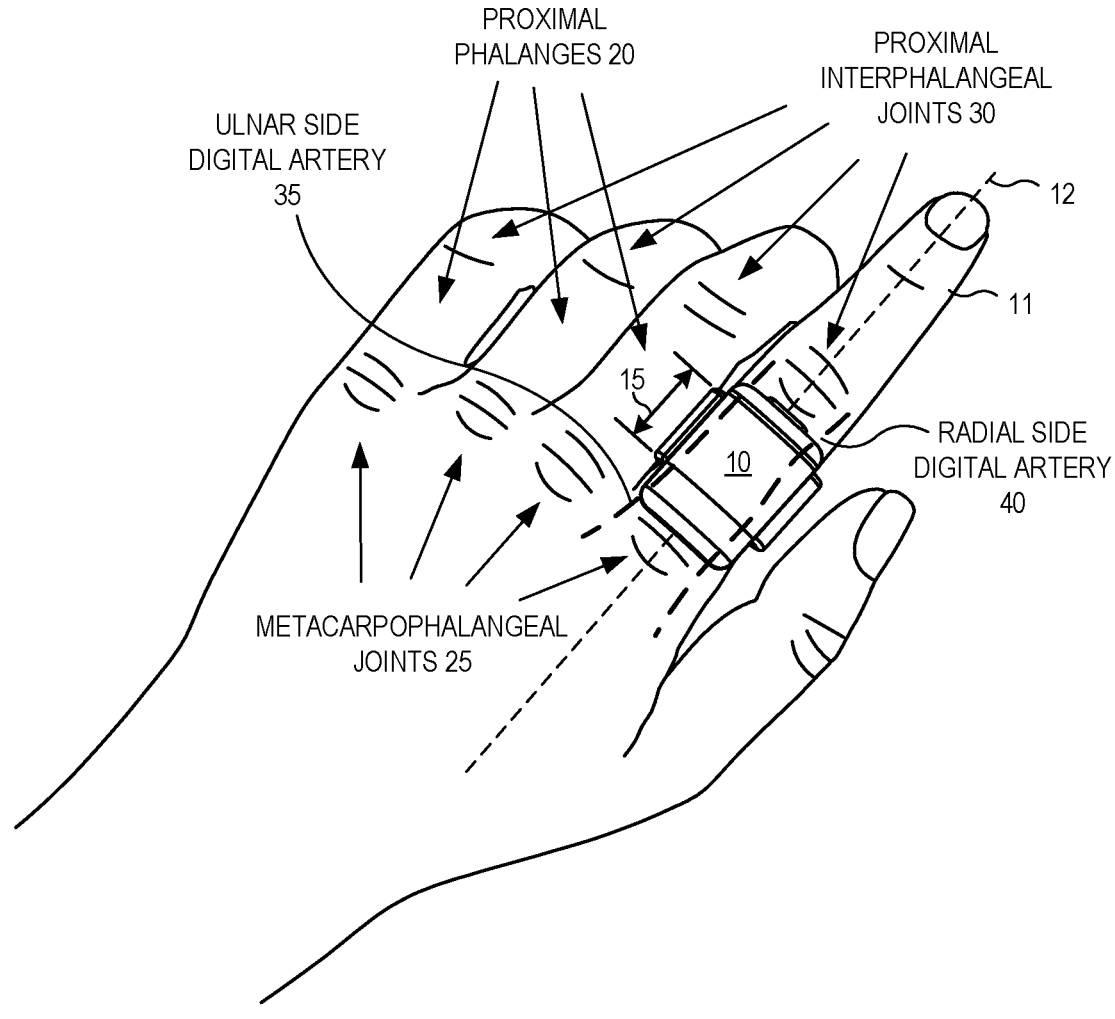
FIG. 1B is a perspective view illustration of wearable blood pressure meter worn on a finger, in accordance with an embodiment of the disclosure.

FIG. 1B is a perspective view illustration of a wearable blood pressure meter 10 worn on a finger 11, in accordance with an embodiment of the disclosure. Blood pressure meter 10 is a non-intrusive and seamless way to meter the blood pressure of a wearer. Blood pressure meter 10 includes a semi-conformable bladder that serves as a reservoir for an incompressible fluid. The incompressible fluid operates as the working fluid coupling the physiological pressure signals to the pressure sensor.

FIG. 1B illustrates blood pressure meter 10 implemented as finger-wearable blood pressure monitor; however, it is contemplated that blood pressure meter 10 may be implemented in other form factors and sizes for sliding over or wearing on other extremities or body parts. These body parts include wrists, upper arms, ankles, toes, legs, or even the neck. Although FIG. 1B illustrates blood pressure meter 10 positioned over a left-hand index finger, it may be configured for use on a right-hand or on other fingers or thumbs of a user.

Blood pressure meter 10 attaches to the user's body part (e.g., finger 11) via a cuff having a size and shape for securing around the body part. The cuff can be fabricated of an inextensible material (e.g., nylon, plastic, metal, etc.) so that it doesn't stretch and dampen the pulsatility signals before reaching the pressure sensor. The cuff cinches around a body part (illustrated as a finger cuff cinched around a finger) for occluding (or partially occluding) an artery within the body part. In various embodiments, the cuff may be manually cinched or automatically actuated via a motor, thereby reducing the cross-sectional area defined by the cuff. In embodiments using a motor, the cuff may be tightened to a preset tension. In some embodiments, a pump may be coupled to the semi-conformable bladder to apply a preset pressure after manually cinching or automatic tightening of the cuff. The pressure applied by the pump causes the semi-conformable bladder to expand an elastic membrane (discussed below) to achieve actuation and occlusion of the artery. Thus, the pressure exerted on the underlying artery may be due to a controlled tightening and/or loosening of the cuff with a motor, a controlled pumping pressure that expands/deflates the elastic membrane, or a combination of both. Of course, the cuff may be replaced with other types of body mounts having other form factors.

The illustrated embodiment of blood pressure meter 10 has a compact form factor with an axial width 15 of the cuff itself fitting over a proximal phalanx 20 of finger 11 between metacarpophalangeal joint 25 and proximal interphalangeal joint 30. This compact form factor provides the user freedom to bend and use finger 11 while wearing blood pressure meter 10, which lends itself well to longer term monitoring of blood pressure without significant user discomfort or disruption to daily activities. The configuration of blood pressure meter 10 illustrated in FIG. 1B obtains blood pressure measurements from either or both of ulnar side digital artery 35 or radial side digital artery 40 running in finger 11. Of course, not all advantages or features need be present in all embodiments. Furthermore, FIG. 1B is merely illustrating a demonstrative finger cuff implementation while the use of an incompressible fluid in a blood pressure meter is equally applicable to other larger meters attached to other body parts (e.g., wrist, upper arm, leg, angle, neck, etc.).

Figure 1C:
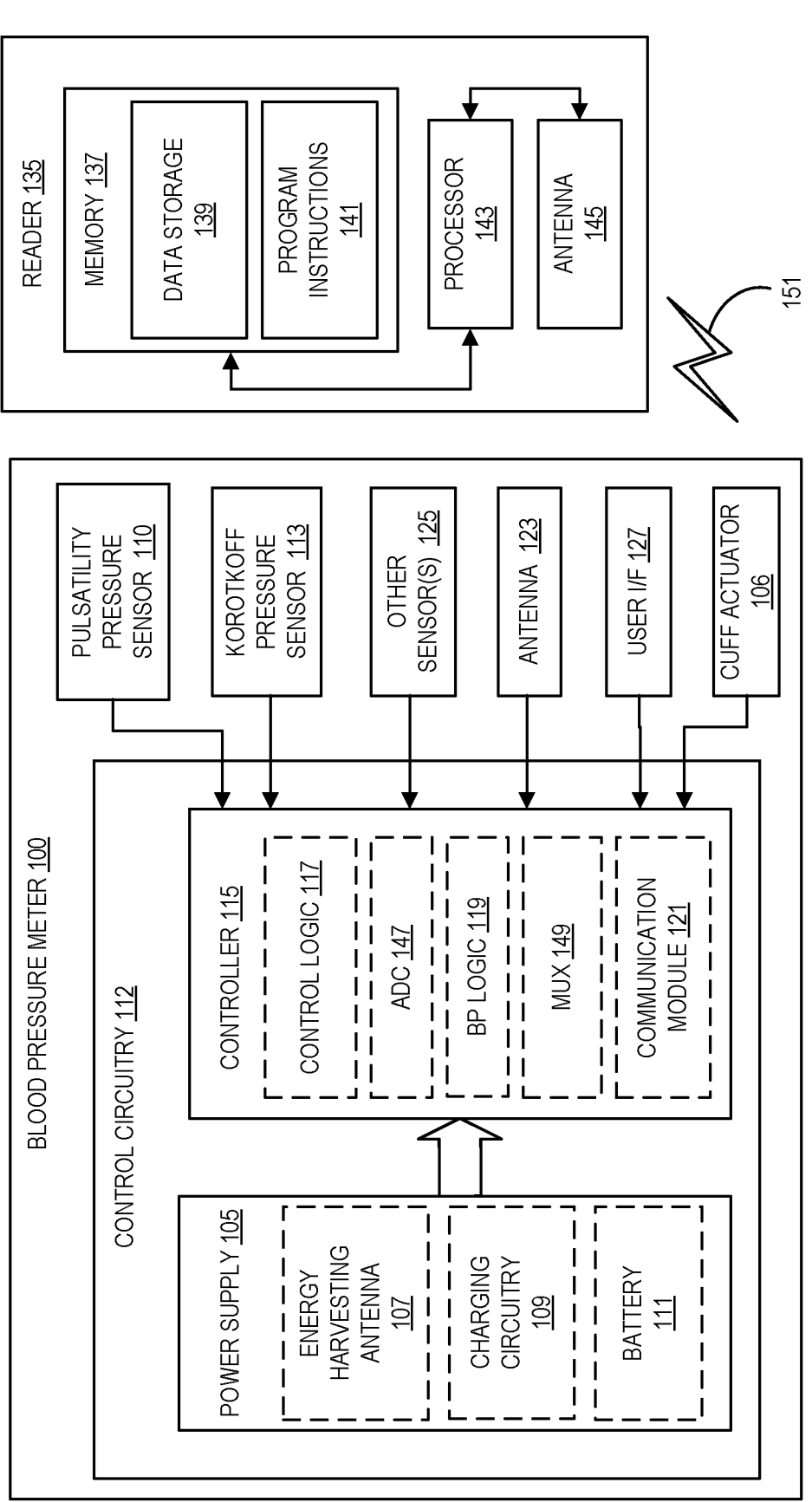
FIG. 1C is a functional block diagram illustrating functional components of a wearable blood pressure meter, in accordance with an embodiment of the disclosure.

FIG. 1C is a functional block diagram illustrating functional electronic components of a wearable blood pressure meter 100, in accordance with an embodiment of the disclosure. Blood pressure meter 100 represents one possible implementation of blood pressure meter 10 illustrated in FIG. 1B. The illustrated embodiment of blood pressure meter 100 includes control circuitry 112, a cuff actuator 106, pulsatility pressure sensor 110, a Korotkoff pressure sensor 113, an antenna 123, other sensors 125, and user interfaces 127. The illustrated embodiment of control circuitry 112 includes a power supply 105 and a controller 115. The illustrated embodiment of power supply 105 includes an energy harvesting antenna 107, charging circuitry 109, and a battery 111. The illustrated embodiment of controller 115 includes control logic 117, blood pressure (BP) logic 119, an Analog-to-Digital Converter (ADC) 147, a multiplexer (MUX) 149, and communication module 121.

Power supply 105 supplies operating voltages to the controller 115 and various other sensors and components of blood pressure meter 100. In the illustrated embodiment, power supply 105 includes battery 111 to power the various embedded electronics, including controller 115. Battery 111 may be inductively charged by charging circuitry 109 and energy harvesting antenna 107. In one embodiment, antenna 123 and energy harvesting antenna 107 are independent antennae, which serve their respective functions of energy harvesting and communications. In another embodiment, energy harvesting antenna 107 and antenna 123 are the same physical antenna that are time shared for their respective functions of inductive charging and wireless communications with reader 135. In yet other embodiments, battery 111 may be charged via a wired port of device 100. Charging circuitry 109 may include a rectifier/regulator to condition the captured energy for charging battery 111 or directly power controller 115 without battery 111.

Controller 115 contains logic to choreograph the operation of the other embedded components. Control logic 117 controls the general operation of blood pressure meter 100, including in some embodiments optionally providing a logical user interface, power control functionality, etc. Additionally, control logic 117 may control the actuation of cuff actuator 106 and receives and records pressure signals from pulsatility pressure sensor 110 and optional Korotkoff Pressure sensor 113, as well as, other data signals from the other sensors 125. For example, other sensors 125 may optionally include a temperature sensor and/or a photoplethysmography (PPG) sensor. ADC 147 receives data from the sensors and converts any received analog data to a digital format and provide the same to control logic 117 and/or BP logic 119. In some embodiments, ADC 147 may be coupled to one or more of pulsatility pressure sensor 110, Korotkoff pressure sensor 113, or other sensors 125 via MUX 149, which controls the inflow of data to the ADC 147. Cuff actuator 106 may be implemented as a body mount that cinches around a body part (or otherwise presses an active area of the semi-conformable bladder against the skin) or a fluid pump that pressurizes the incompressible fluid to press an elastic membrane in the active area against the skin over an artery.

BP logic 119 receives the measurements (e.g., pressure measurements, temperature measurements, etc.) from pulsatility pressure sensor 110, Korotkoff pressure sensor 113, or other sensors 125 and converts the measurements into equivalent pressure values. The pressure values may be in mmHg, for example. The pressure values may further be converted into pressure waveforms (e.g., see FIG. 1A) that may be analyzed in either the time or frequency domains to determine mean arterial pressure, systolic blood pressure, and/or diastolic blood pressure at the digital artery. In some embodiments, the pulsatility signals may be converted from a first waveform type (e.g., pressure at the digital artery) to a second waveform type (e.g., pressure at a brachial artery). BP logic 119 may analyze the waveforms to identify arterial pulses and subsequently determine or estimate blood pressure. Blood pressure meter 100 may use a variety of techniques such as oscillometry, auscultation, or applanation tonometry to estimate a user's blood pressure at an artery in an extremity (e.g., digital artery of a finger), which may subsequently be converted to a clinical or brachial blood pressure with a transfer function and/or a machine learning algorithm.

For applanation tonometry, cuff actuator 106 presses an active area of a semi-conformable bladder into the body part over an artery, which may deform the artery. The artery may or may not be deformed to occlusion. As the pressure applied by the body part is slowly reduced, the artery may slowly convert back to a normal shape, and may pass through a point where the internal pressure equals the external pressure exerted on the artery by the active area. This point may occur when a local radius of the artery approaches infinity (i.e., flattens). In this state, e.g., with the local region of the artery being flat, the blood flow variations in the artery due to heart beats may cause the flat area of the artery to experience pressure fluctuations (e.g., arterial pulses). A maximum fluctuation, representing one of the arterial pulses having a pulse amplitude larger than the pulse amplitude of any other one of the arterial pulses, may occur at the flat condition. The pressure fluctuations may decrease when the local region is not quite flat. While the above operation was discussed in terms of a controlled reduction in pressure applied between a body part and an active area of a semi-conformable bladder, the operation may alternatively be performed using a controlled increase in pressure and the pressure changes may be measured during the controlled increase.

Pulsatility pressure sensor 110 is operated to sense the above-mentioned pressure fluctuations or arterial pulses incident upon an active area of a semi-conformable bladder of blood pressure meter 100. An incompressible fluid is provided within the semi-conformable bladder to couple and propagate these pressure signals from the user's skin to the pulsatility pressure sensor 110. Pulsatility pressure sensor 110 may be a waterproof sensor adapted for direct mechanical coupling to the incompressible fluid. In various embodiments, pulsatility pressure sensor 110 is designed, or low pass filtered, to focus on the lower frequencies (e.g., 0 to 20 Hz) generated by the human heart.

In some embodiments, BP logic 119 may receive sound recordings from Korotkoff pressure sensor 113, which is essentially operating as a microphone also coupled via the incompressible fluid, to implement auscultatory blood pressure estimation. In one embodiment, the pulsatility pressure sensor 110 and Korotkoff pressure sensor 113 may be implemented with the same pressure sensor, but the output data high pass filtered to extract the Korotkoff sounds. The Korotkoff sounds typically occur in frequency bands up to a few hundred hertz. BP logic 119 analyzes the sound recordings in relation to pressure data received from pulsatility pressure sensor 110 to determine a baseband pressure when Korotkoff sounds begin and end. If the pressure is decreasing during this time from an occluded state of the artery, the pressure corresponding to the beginning of the Korotkoff sounds may be an estimate of the systolic blood pressure, whereas the pressure corresponding to the ending of the Korotkoff sounds may be an estimate of the diastolic blood pressure.

In some embodiments, BP logic 119 may determine the mean arterial pressure (MAP), systolic blood pressure (SBP), and diastolic blood pressure (DBP) using oscillometry. The determination of the mean arterial pressure, systolic blood pressure, and diastolic blood pressure may be similar to applanation tonometry techniques. For example, the pressure signals from pulsatility pressure sensor 110 may measure pressure changes due to blood flow in the digital artery. The pressure oscillations may start small, increase to a maximum amplitude, and reduce. Similar to the applanation tonometry technique, the applied pressure at maximum amplitude may be an estimate of the mean arterial pressure. From the measured pressure oscillations, BP logic 119 may determine the mean arterial pressure, the systolic blood pressure, and the diastolic pressure. The systolic blood pressure and diastolic blood pressure can be calculated from the measured mean arterial pressure through one or more regressions (e.g., linear regression).

In some embodiments, BP logic 119 may perform BP estimations using all three techniques. The BP estimations from the three different techniques can then be compared to determine a closest estimation of the user's BP at the peripheral artery in the extremity. Additionally, or alternatively, BP logic 119 may utilize the blood pressure estimates from the oscillometry and auscultatory techniques as reference data to confirm and/or verify the accuracy of the blood pressure estimate from pulsatility pressure sensor 110 determined with regularized regression modeling or a machine learning algorithm.

Control logic 117 may receive diagnostic data from other sensors 125, which may include a temperature sensor, accelerometer, photoplethysmograph (PPG), and/or a microphone. The data may be analyzed to determine if any of the measurements are outside of established thresholds and, if so, respond accordingly. For example, if accelerometer data shows that the body part was moving more than desired during a blood pressure reading, control logic 117 may reject that reading. Additionally, control logic 117 may determine the user's heart rate (HR), respiratory rate (RR), and/or oxygen saturation (SpO2) based on PPG sensor data. Lastly, temperature data may be used to scale or offset the baseband pressure reading output from pulsatility pressure sensor 110 to account for thermal expansion of the incompressible fluid within the semi-conformable bladder.

Communication module 121 provides communication protocols for wireless communication with reader 135 via antenna 123. In one embodiment, communication module 121 provides backscatter communication via antenna 123 when in the presence of an electromagnetic field 151 output from reader 135. In one embodiment, communication module 121 operates as a smart wireless radio-frequency identification ("RFID") tag that modulates the impedance of antenna 123 for backscatter wireless communications. The various logic modules of controller 115 may be implemented in software/firmware executed on a general purpose microprocessor, in hardware (e.g., application specific integrated circuit), or a combination of both. Of course, communication module 121 and antenna 123 may implement other communication standards, such as WiFi, Bluetooth, etc.

The illustrated embodiment also includes reader 135 with a processor 143, an antenna 145, and memory 137. Memory 137 includes data storage 139 and program instructions 141. As shown, reader 135 may be disposed outside of device 100, but may be placed in its proximity to charge device 100, send instructions to device 100, and/or extract data from device 100. In one embodiment, reader 135 resembles a handheld portable device, such as a smartphone, a tablet, a laptop, or otherwise.

Figure 2A:
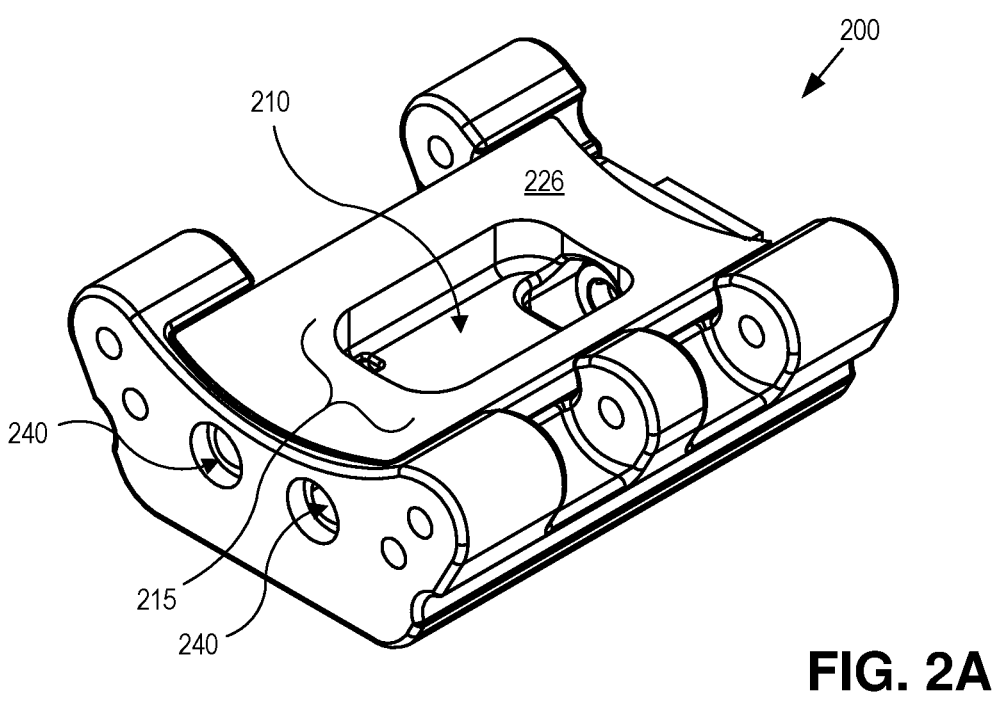
FIG. 2A is a bottom perspective view illustration of a semi-conformable bladder illustrating an active area defined by an aperture through a rigid housing, in accordance with an embodiment of the disclosure.
Figure 2B:
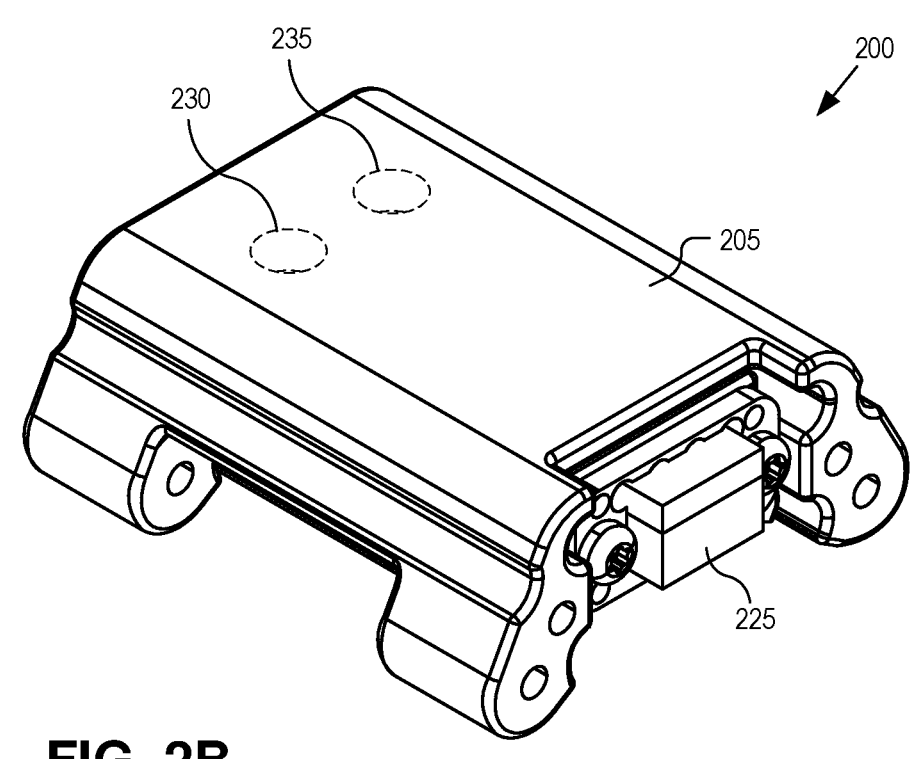
FIG. 2B is a top perspective view illustration of the semi-conformable bladder, in accordance with an embodiment of the disclosure.
Figure 2C:
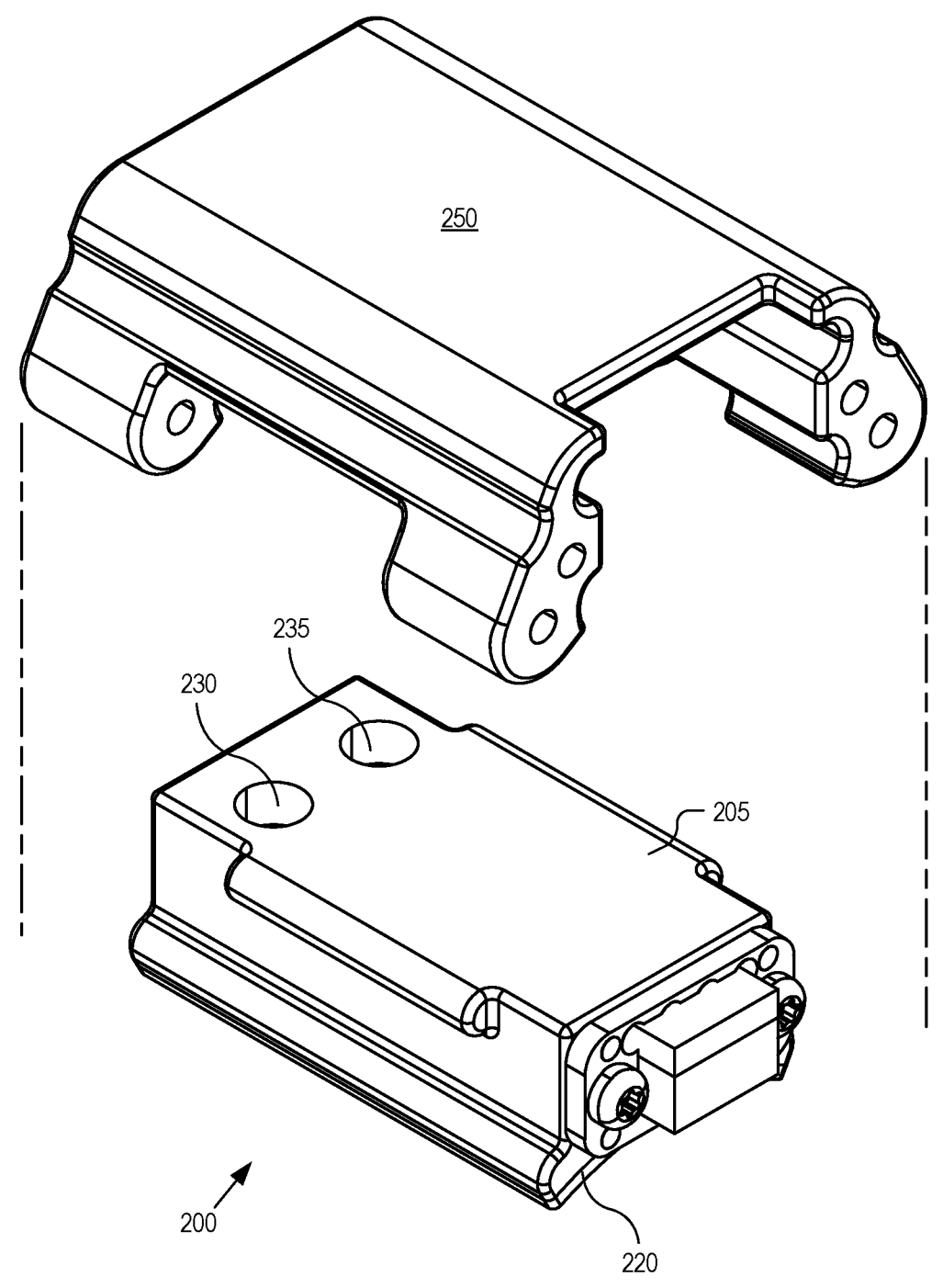
FIG. 2C is a top exploded view illustration of the semi-conformable bladder, in accordance with an embodiment of the disclosure.
Figure 2D:
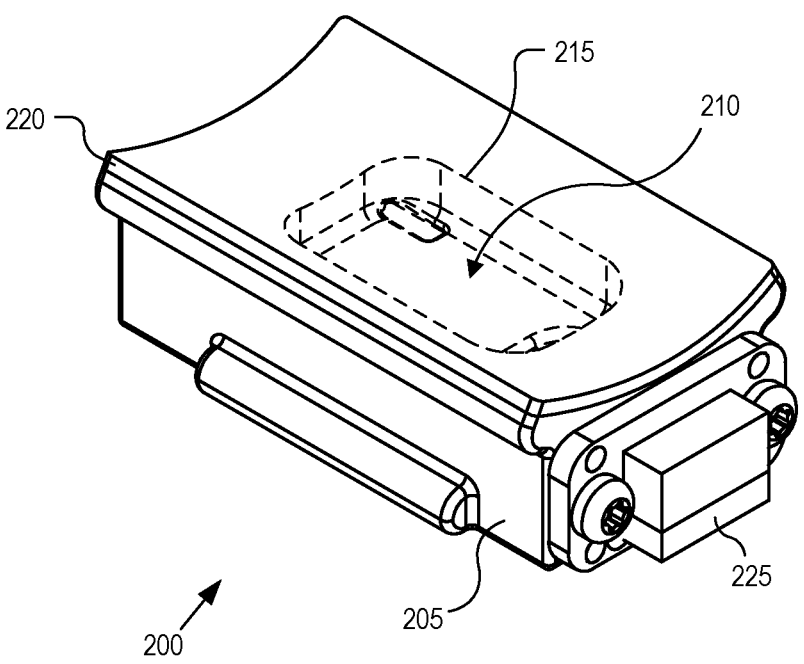
FIG. 2D is a bottom perspective view illustration of the semi-conformable bladder with an elastic membrane extending across the aperture, in accordance with an embodiment of the disclosure.
Figure 2E:
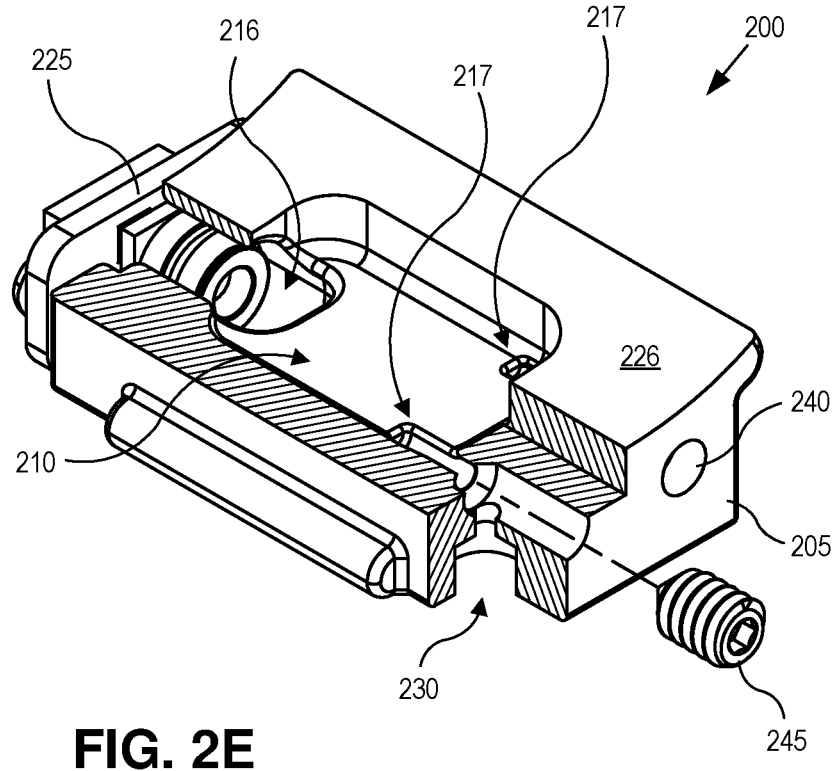
FIG. 2E is a cutaway perspective view illustration of the semi-conformable bladder showing an internal cavity and channels, in accordance with an embodiment of the disclosure.

FIGS. 2A-E illustrate a semi-conformable bladder 200 for use with blood pressure meters 10 or 100, in accordance with an embodiment of the disclosure. FIGS. 2A & 2D are bottom-side perspective views, FIGS. 2B & 2C are topside perspective views, and FIG. 2E is a cutaway perspective view all of the same semi-conformable bladder 200, in accordance with an embodiment of the disclosure. It should be appreciated that semi-conformable bladder 200 assumes a size and shape for wearing on a finger; however, the size and form factor may be adapted to wearing on a wrist, upper arm, angle, toe, neck, or otherwise where an artery is sufficiently close to the skin surface to sense arterial pulses.

The illustrated embodiment of semi-conformable bladder 200 includes a rigid housing 205 defining a cavity 210, which is exposed by an aperture 215 through rigid housing 205. The aperture 215 is overlaid with an elastic membrane 220 (see FIG. 2D). In the illustrated embodiment, a sensor module 225 is mounted directly and fixedly to rigid housing 205. Rigid housing 205 includes a rigid interface surface 226 that is a curved surface surrounding aperture 215 and which may have a curvature approximately matching the body part against which semi-conformable bladder 200 is pressed. The illustrated embodiment of rigid housing 205 further includes a fill port 230, a bleed port 235, and valve ports 240 that accept plugs 245 for opening/closing fill port 230 and bleed port 235. Valve ports 240 and plugs 245 may collectively be referred to as "valves." Finally, the illustrated embodiment further includes a cover 250 for attaching to a body mount.

Semi-conformable bladder 200 serves as a reservoir for an incompressible fluid, such as a liquid (e.g., water, mineral oil, etc.). Semi-conformable bladder 200 includes rigid housing 205 and elastic membrane 220. Semi-conformable bladder 200 is referred to as "semi-conformable" because rigid housing 205 rigidly confines only a portion of cavity 210 while elastic membrane 220 elastically confines the other portion. As such, elastic membrane 220 conforms to the body part while rigid housing 205 does not. In the illustrated embodiment, rigid housing 205 rigidly confines the incompressible fluid within cavity 210 on five sides and elastic membrane 220 confines the incompressible fluid only on a single side. This configuration increases the signal-to-noise ratio and the pressure sensitivity to pressure signals incident through elastic membrane 220.

Rigid housing 205 may be fabricated of a variety of rigid, waterproof materials including plastic, resin, metal, composites, or otherwise. Elastic membrane 220 may be fabricated of a variety of elastic materials such as nitrile, thermoplastic elastomers (TPE), thermoplastic polyurethane (TPU), or other biocompatible and extensible materials. Example incompressible fluids include water, mineral oil, or otherwise. Both liquids have a density and acoustic impedance that closely matches blood. Mineral oil is well suited as a working fluid for semi-conformable bladder 200 due to its stability, low thermal coefficient of expansion, low vapor pressure that doesn't easily evaporate through elastic membrane 220, and is otherwise compatible with (e.g., doesn't corrode or degrade) pressure sensor module 225 and elastic membrane 220.

Rigid housing 205 includes rigid interface surface 226, which surrounds aperture 215 and is referred to as the "inactive area." The area including aperture 215 is referred to as the "active area." The inactive area serves to immobilize and/or stabilize the body part surrounding the active area and otherwise isolate the active area from edge effects and other noise resulting from the pressure boundary at the outer edge of rigid interface surface 226. The inactive area is intended to apply uniform pressure with the active area, but otherwise provides a buffer from the outer edge where the applied pressure from rigid housing 205 and the body mount steps up from zero. In the illustrated embodiment, rigid interface surface 226 is a curved surface that approximates a curvature of the body part. The active area as defined by aperture 215 is overlaid by elastic membrane 220 and serves as the region for uniform application of pressure against the skin and sensing pressure signals emanating from an artery in the body part below the patient's skin directly beneath the active area. Elastic membrane 220 conforms to the body part allowing the arterial pulse pressure waves to propagate across the skin-membrane boundary into the incompressible fluid and therethrough to the pressure sensor module 225.

Referring to FIG. 2E, cavity 210 includes a central cavity directly beneath aperture 215 as well as a sensor channel 216 that extends to pressure sensor module 225 and fill and bleed channels 217 that extend to fill port 230 and bleed port 235. Cavity 210 may assume a variety of different sizes and shapes; however, if the volume of cavity 210 is too small, the active area may not be sufficient compliant to conform to the patient's body part while overly large volumes may suffer increased pressure deviations due to thermal expansion. In one embodiment, the volume of cavity 210 is: 100 mm$^3$ and the area of aperture 215 is: 36 mm$^2$. Other dimensions may be implemented.

Sensor channel 216 extends cavity 210 immediately under aperture 215 to pressure sensor module 225 such that the incompressible fluid entirely fills the volume without voids or air bubbles. Pressure sensor module 225 includes pulsatility pressure sensor 110 and optionally Korotkoff pressure sensor 113 and/or a temperature sensor. These sensors may be individual units or integrated into a common structural module. The sensors physically/thermally couple to the incompressible fluid, and by extension, to elastic membrane 220. Pressure sensor module 225 may be mounted directly and fixedly to rigid housing 205 (illustrated) or remotely attached to rigid housing 205 via a lanyard having an inextensible channel extending from sensor channel 216 and filled with the same incompressible fluid (not illustrated). In one embodiment, controller 115 is integrated with or otherwise attached to (e.g., via a mounting substrate) pressure sensor module 225. Of course, controller 115 may also be remotely attached via a cable or mounted to a backside, or elsewhere, of rigid housing 205. In yet other embodiments, controller 115 may be remotely located and wirelessly coupled to receive sensor data from pulsatility pressure sensor 110, Korotkoff pressure sensor 113, or other sensors 125. Though not illustrated, a PPG sensor may be mounted in inactive region 225 facing the body part, or alternatively, attached to a cuff for cinching around the body part.

Figure 3:
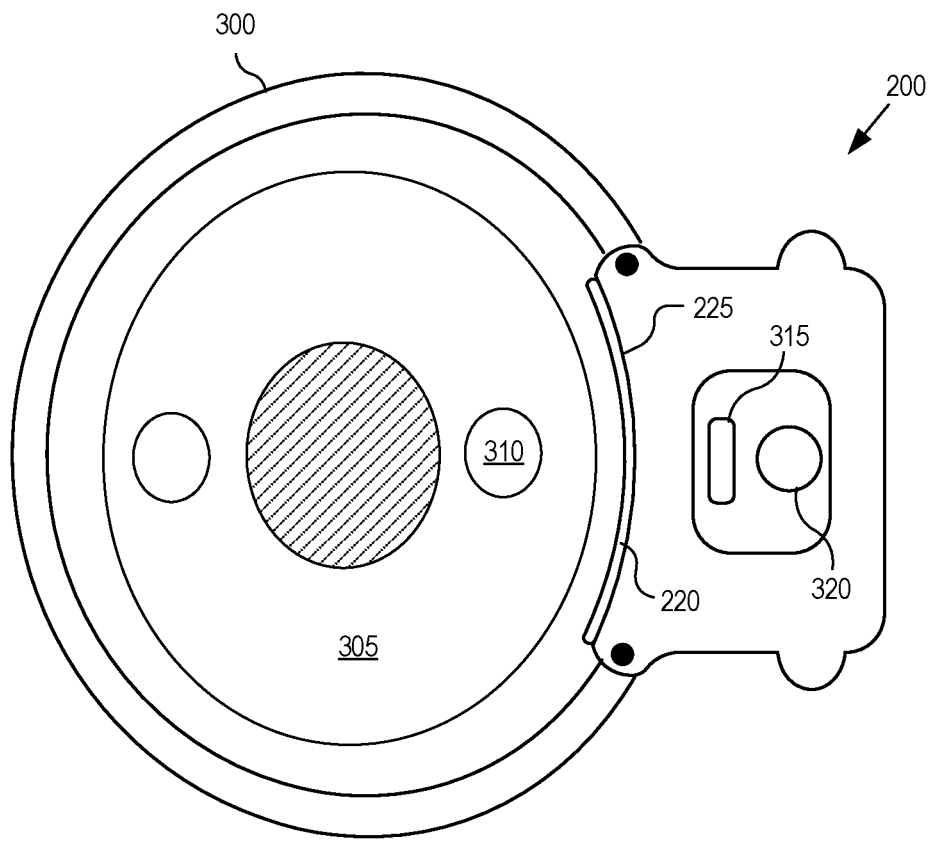
FIG. 3 illustrates an example body mount in the form of an inextensible cuff for securing the wearable blood pressure meter to a body part, in accordance with an embodiment of the disclosure.

FIG. 3 illustrates an example body mount 300 for securing semi-conformable bladder 200 to a body part 305. In the illustrated embodiment, body mount 300 is an inextensible cuff that cinches around body part 305 (e.g., finger). Body mount 300 presses the active area and inactive area of rigid interface surface 226 against the skin surface of body part 305 directly over artery 310 (e.g., digital artery 40). As illustrated, rigid interface surface 226 has a curvature that approximates the local curvature of body part 305. Additionally, the rigid housing may support electronics for a communication/charging port 315 and a user interface button 320. Other communication and interface arrangements may be implemented.

Figure 4:
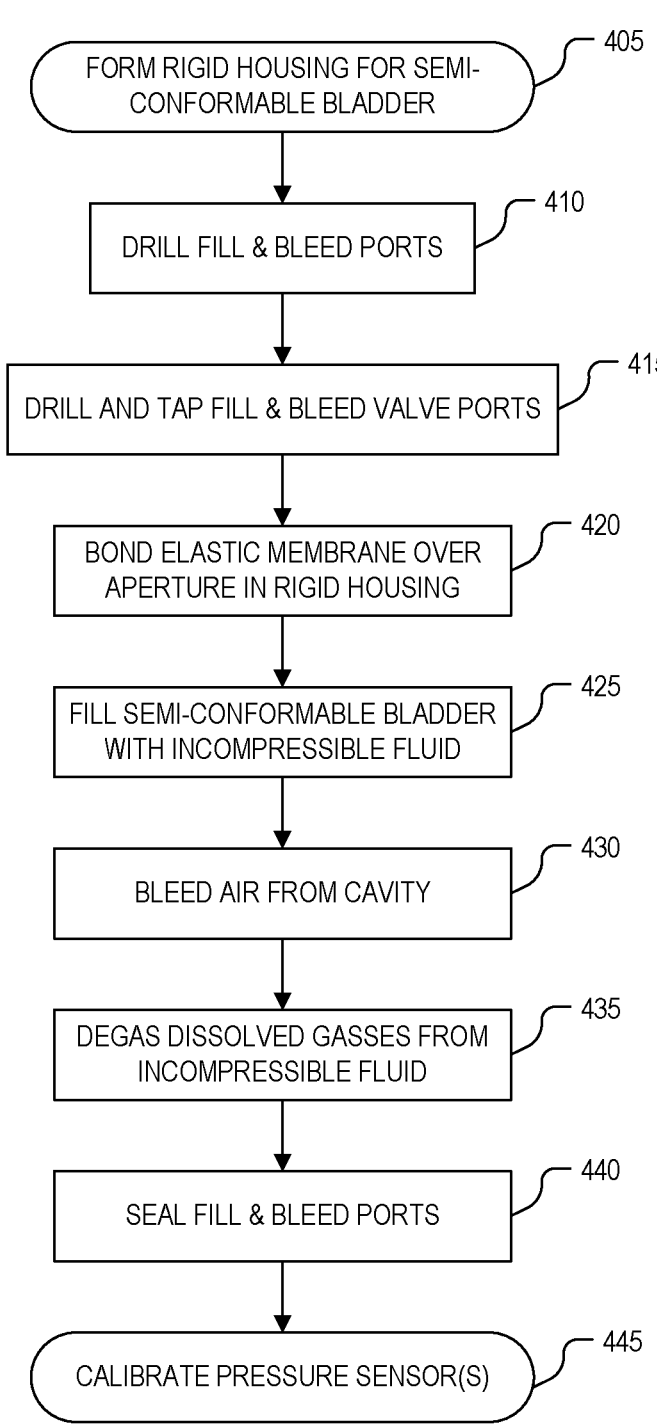
FIG. 4 is a flow chart illustrating a process for fabrication and assembly of the wearable blood pressure meter, in accordance with an embodiment of the disclosure.

FIG. 4 is a flow chart illustrating a process 400 for fabrication and assembly of wearable blood pressure meter 10, in accordance with an embodiment of the disclosure. The order in which some or all of the process blocks appear in process 10 should not be deemed limiting. Rather, one of ordinary skill in the art having the benefit of the present disclosure will understand that some of the process blocks may be executed in a variety of orders not illustrated, or even in parallel.

In a process block 405, rigid housing 205 of semi-conformable bladder 200 is fabricated. Fabrication may include injection molding, 3D printing, CNC machining or otherwise. Fill and bleed ports 230/235 are drilled (process block 410) while valve ports 240 are drilled and tapped (process block 415). With valve ports 240 tapped, threaded plugs 245 can be partially threaded into the holes. In a process block 420, elastic membrane 220 is bonded to rigid interface surface 226 and extends over aperture 215. Bonding may include the use of an adhesive, hot welding, or otherwise.

With semi-conformable bladder 200 formed, cavity 210 is filled with the incompressible fluid (e.g., mineral oil) through fill port 230 (process block 425). A syringe may be used for the filling activity. As the incompressible fluid is filled into cavity 210, air is pushed out through bleed port 235 (process block 430). After filling cavity 210 with the incompressible fluid but prior to sealing off the fill and bleed valves, semi-conformable bladder 200 may be placed under vacuum to draw out dissolved gasses thereby degassing the incompressible fluid (process block 435). In a process block 440, the fill and bleed valves are closed via fully threading and seating plugs 245 against the shoulders of fill and bleed channels 217. Finally, in a process block 445, pressure sensor module 225 may execute diagnostic and calibration routines to ensure the blood pressure meter is fully operational and the pressure sensors correctly calibrated.

FIGS. 5A-C illustrate a semi-conformable bladder 500, in accordance with another embodiment of the disclosure. FIG. 5A illustrates a frontside of semi-conformable bladder 500, FIG. 5B illustrates a backside of semi-conformable bladder 500, and FIG. 5C illustrates a cross-sectional view of the same. Semi-conformable bladder 500 is similar to semi-conformable bladder 200 with the following notable differences. The structural differences of semi-conformable bladder 500 relative to semi-conformable bladder 200 facilitate another fill process for injecting the incompressible fluid into the internal cavity defined by the semi-conformable bladder.

Semi-conformable bladder 500 includes a rigid housing 505 and an elastic membrane 520 with an intervening overmold layer 506. In one embodiment, elastic membrane 520 and overmold layer 506 are formed of the same or common material (e.g., TPE, TPU, etc.) with elastic membrane 520 being a thin film and overmold layer 506 being a thicker structural layer that mates to the rigid housing 505. Overmold layer 506 also includes a rigid interface surface supported by rigid housing 505 that is a curved surface surrounding aperture 515 and which may have a curvature approximately matching the body part against which semi-conformable bladder 500 is pressed. In the illustrated embodiment, pressure sensor module 225 is moved from an end cap surface (as illustrated in FIG. 2D) to the backside surface of rigid housing 505.

Figure 6A:
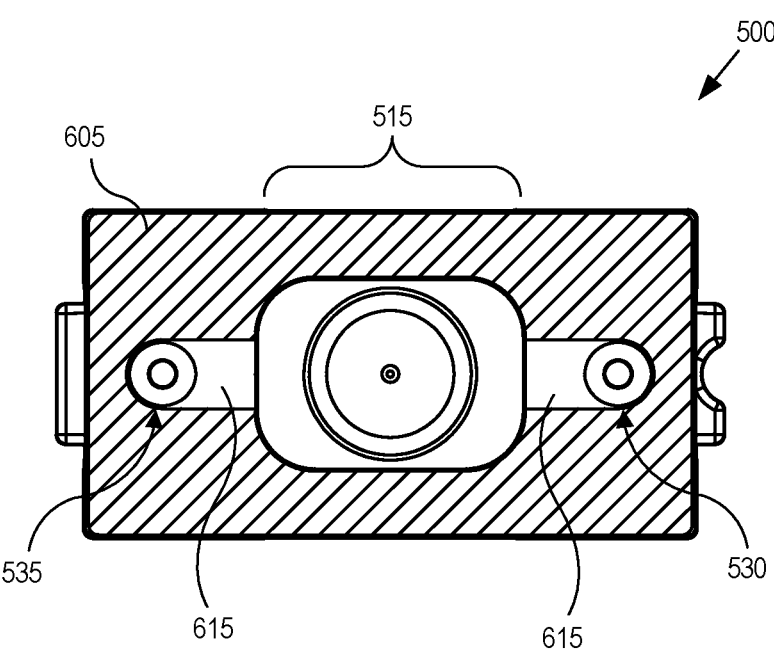
FIG. 6A is a plan view illustrating fill channels formed between an elastic membrane and an overmold layer during assembly of the semi-conformable bladder, in accordance with the second embodiment of the disclosure.
Figure 6B:
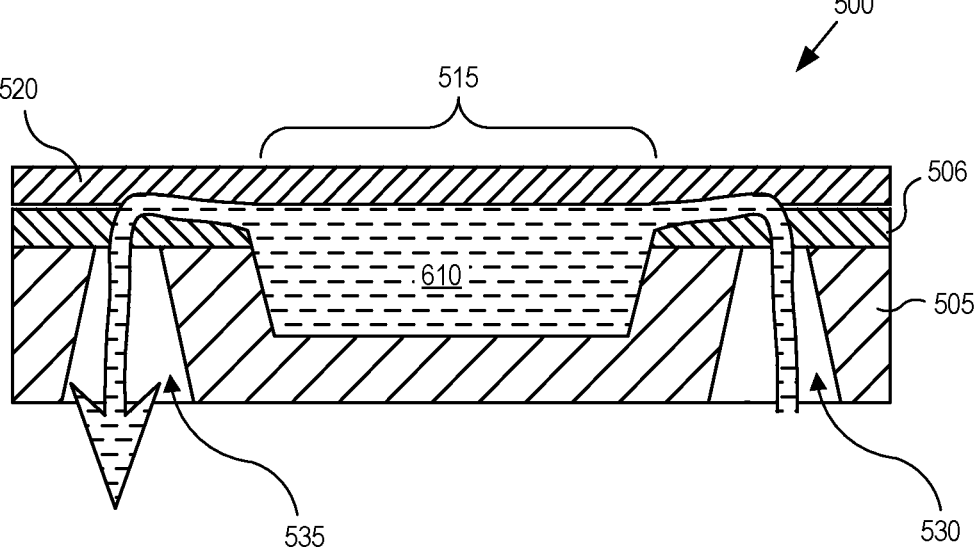
FIG. 6B is a cross-sectional illustration of the fill channels, in accordance with the second embodiment of the disclosure.
Figure 6C:
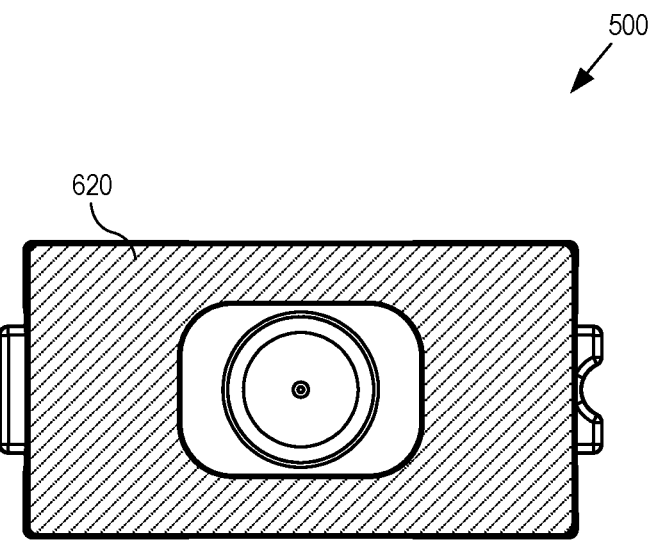
FIG. 6C is a plan view illustrating the fill channels sealed off, in accordance with the second embodiment of the disclosure.

FIGS. 6A-C illustrate the process for filling the incompressible fluid into semi-conformable bladder 500. During assembly of semi-conformable bladder 500, after overmold layer 506 has been molded onto rigid housing 505, elastic membrane 520 is placed over overmold layer 506 and the two layers are fused together with a heated press head (not illustrated). Overmold layer 506 operates as a selective bonding layer between elastic membrane 220 and rigid housing 505. The heated press head has a curvature that matches the curvature of the interface surface and a footprint shape that excludes aperture 515 and fill channels 615. In other words, the heated press head fuses elastic membrane 520 to overmold layer 506 in a pattern 605 that leaves fill channels 615 unfused, thereby permitting fluid passage from fill port 530 into cavity 610, and out bleed port 535. A separate filling fixture may be used that mates to fill port 530 and bleed port 535 to facilitate fluid injection without introduction of air bubbles. After the incompressible fluid has been injected, another heated press plate fuses fill channels 615 closed forming a fuse pattern 620 (see FIG. 6C) between overmold layer 506 and elastic membrane 520.

Some of the processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A wearable blood pressure meter, comprising:
a semi-conformable bladder serving as a reservoir for an incompressible fluid, the semi-conformable bladder including:
    a rigid housing defining a cavity within which the incompressible fluid is rigidly constrained by the rigid housing, the rigid housing including an aperture through the rigid housing into the cavity;
    an elastic membrane extending across the aperture for elastically constraining the incompressible fluid at the aperture, wherein a portion of the elastic membrane that extends across the aperture is configured to conform to a body part when the elastic membrane is pressed against the body part; and
    an overmold layer disposed between the elastic membrane and the rigid housing, wherein the overmold layer is formed of a common material as the elastic membrane but having a greater thickness than the elastic membrane; and a pressure sensor mechanically coupled to the incompressible fluid to measure pressure signals emanating from an artery within the body part and propagated through the elastic membrane and the incompressible fluid to the pressure sensor.

2. The wearable blood pressure meter of claim 1, further comprising:
a body mount attached to the rigid housing and adapted to press the elastic membrane against the body part when the wearable blood pressure meter is worn.

3. The wearable blood pressure meter of claim 2, wherein the body mount comprises an inextensible cuff having a size and a shape for extending around the body part having the artery and securing the semi-conformable bladder to the body part.

4. The wearable blood pressure meter of claim 1, wherein the rigid housing includes a rigid interface surface surrounding the aperture, wherein the rigid interface surface is configured to press against the body part when the wearable blood pressure meter is worn, the rigid interface surface operating as an inactive area that immobilizes or stabilizes a portion of the body part that immediately surrounds the aperture, wherein the aperture defines an active area for measuring the pressure signals through the elastic membrane.

5. The wearable blood pressure meter of claim 4, wherein the rigid interface surface comprises a curved surface.

6. The wearable blood pressure meter of claim 1, wherein the rigid housing rigidly confines the incompressible fluid on five sides of the cavity and the elastic membrane elastically confines the incompressible fluid on a single side of the cavity.

7. The wearable blood pressure meter of claim 1, wherein the pressure sensor comprises a first pressure sensor adapted to sense pulsatility signals below 20 Hz, the wearable blood pressure meter further comprising:
a second pressure sensor mechanically coupled to the incompressible fluid and adapted to measure Korotkoff sounds having a higher frequency than the pulsatility signals.

8. The wearable blood pressure meter of claim 1, wherein the pressure sensor is mounted directly and fixedly to the rigid housing.

9. The wearable blood pressure meter of claim 1, wherein the pressure sensor is indirectly attached to the rigid housing via an inextensible channel coupled to the cavity and filled with the incompressible fluid.

10. The wearable blood pressure meter of claim 1, further comprising:
a temperature sensor mounted to the rigid housing to measure a temperature of the incompressible fluid.

11. The wearable blood pressure meter of claim 10, further comprising:
a controller coupled to the pressure sensor and to the temperature sensor, wherein the controller includes logic that when executed by the controller causes the wearable blood pressure meter to perform operations including:
    recording the pressure signals and the temperature;
    scaling the pressure signals to account for changes in the temperature; and
    determine a blood pressure measurement based upon the pressure signals as scaled for the temperature.

12. The wearable blood pressure meter of claim 1, wherein the rigid housing comprises:
a fill port for injecting the incompressible fluid into the cavity;

a bleed port for bleeding a gas from the cavity; and valves for opening and closing the fill and bleed ports.

13. The wearable blood pressure meter of claim 1, wherein the incompressible fluid comprises mineral oil and the elastic membrane comprises at least one of a nitrile material, a thermoplastic elastomer, or a thermoplastic polyurethane.

14. A wearable sensor system, comprising:

a liquid;

a rigid housing defining a cavity within which the liquid is rigidly constrained by the rigid housing, the rigid housing including an aperture through the rigid housing into the cavity and a rigid interface surface surrounding the aperture;

an elastic membrane extending across the aperture for elastically constraining the liquid at the aperture and wherein a portion of the elastic membrane that extends across the aperture is configured to conform to a body part when the elastic membrane is pressed against the body part;

an overmold layer disposed over the rigid interface surface surrounding the aperture and intervening between the elastic membrane and the rigid housing, wherein the overmold layer is formed of an elastic material having a greater thickness than that of the elastic membrane;

an inextensible cuff attached to the rigid housing and adapted to hold the rigid housing against the body part over an artery within the body part; and a pressure sensor mechanically coupled to the liquid to measure pressure signals emanating from the artery and propagated through the elastic membrane and the liquid to the pressure sensor.

15. The wearable sensor system of claim 14, wherein the rigid interface surface is configured to press against the body part when the wearable blood pressure meter is worn and the rigid interface surface operates as an inactive area that immobilizes or stabilizes a portion of the body part that immediately surrounds the aperture, wherein the aperture defines an active area for measuring the pressure signals through the elastic membrane.

16. The wearable sensor system of claim 14, wherein the rigid housing rigidly confines the liquid on five sides of the cavity and the elastic membrane elastically confines the liquid on a single side of the cavity.

17. The wearable sensor system of claim 14, wherein the pressure sensor comprises a first pressure sensor adapted to sense pulsatility signals below 20 Hz, the wearable blood pressure meter further comprising:

a second pressure sensor mechanically coupled to the liquid and adapted to measure Korotkoff sounds.

18. The wearable sensor system of claim 14, wherein the pressure sensor is mounted directly and fixedly to the rigid housing.

19. The wearable sensor system of claim 14, further comprising:

a temperature sensor mounted to the rigid housing to measure a temperature of the liquid.

20. The wearable sensor system of claim 19, further comprising:

a controller coupled to the pressure and to the temperature sensor, wherein the controller includes logic that when executed by the controller causes the wearable sensor system to perform operations including:

recording the pressure signals and the temperature;

scaling the pressure signals to account for changes in the temperature; and determine a blood pressure measurement based upon the pressure signals as scaled for the temperature.

\* \* \* \* \*